(12) United States Patent
Furue et al.

(10) Patent No.: US 7,923,245 B2
(45) Date of Patent: Apr. 12, 2011

(54) MEDIUM FOR ES CULTURING

(76) Inventors: Miho Furue, Yokosuka (JP); Tetsuji Okamoto, Hiroshima (JP); Makoto Asashima, Tokyo (JP)

( * ) Notice: Subject to any disclaimer, the term of this patent is extended or adjusted under 35 U.S.C. 154(b) by 1015 days.

(21) Appl. No.: 10/584,371

(22) PCT Filed: Dec. 27, 2004

(86) PCT No.: PCT/JP2004/019818
§ 371 (c)(1),
(2), (4) Date: May 1, 2007

(87) PCT Pub. No.: WO2005/063968
PCT Pub. Date: Jul. 14, 2005

(65) Prior Publication Data
US 2008/0050817 A1    Feb. 28, 2008

(30) Foreign Application Priority Data
Dec. 26, 2003  (JP) ................................ 2003-434035

(51) Int. Cl.
*C12N 5/00* (2006.01)
*C12N 5/02* (2006.01)
*A01N 63/00* (2006.01)

(52) U.S. Cl. ........ 435/375; 435/325; 435/366; 435/383; 435/395; 435/404; 435/405; 435/406; 435/407

(58) Field of Classification Search .................. 435/325, 435/375, 366, 383, 395, 404, 405, 406, 407
See application file for complete search history.

(56) References Cited

U.S. PATENT DOCUMENTS

| | | |
|---|---|---|
| 6,150,163 A | 11/2000 | McPherson et al. |
| 2003/0096414 A1 | 5/2003 | Ciccarone et al. |
| 2003/0211604 A1 | 11/2003 | Brown |

FOREIGN PATENT DOCUMENTS

| | | |
|---|---|---|
| JP | 2001-138021 | 4/2003 |
| WO | WO 95/06112 | 3/1995 |
| WO | WO 97/34999 | 9/1997 |
| WO | WO 98/04681 | 2/1998 |
| WO | WO 98/30679 | 7/1998 |
| WO | WO 99/20741 | 4/1999 |
| WO | WO 02/066603 | 8/2002 |
| WO | WO 02/077202 | 10/2002 |
| WO | WO 03/064598 | 8/2003 |

OTHER PUBLICATIONS

International Search Report for PCT/JP2004/019818 completed Feb. 8, 2005.
Supplementary Search Report for EP 04 80 8168.
Johansson et al., "Evidence for Involvement of Actvin A and Bone Morphogenetic Protein 4 in Mammalian Mesoderm and Hematopoietic Development," *Molecular and Cellular Biology*, Jan. 1995, pp. 141-151, vol. 15(1).

*Primary Examiner* — Leon B Lankford
(74) *Attorney, Agent, or Firm* — Alston & Bird LLP

(57) ABSTRACT

The present invention discloses a medium for a serum-free medium capable of culturing ES cells for a long period while maintaining their undifferentiated state without using feeder cells, and a basal medium for producing the medium thus described. The basal medium of the present invention is characterized by that it has composition shown by Table I. Further, the present invention discloses a medium for ES cells produced with the basal medium.

5 Claims, 3 Drawing Sheets

MEDIUM FOR ES CULTURING

TECHNICAL FIELD

The present invention relates to a basal medium for preparing a medium for culturing ES cells of mammals.

BACKGROUND ART

Embryonic stem (ES) cells are in an undifferentiated state and have an ability to develop into any type of differentiated cells in vitro in developmental processes of living organisms. It is known that the self-renewal ability and the undifferentiated state of ES cells can be maintained by using a culture medium supplemented with fetal bovine serum in the presence of feeder cells or LIF (Zandstra, P. W., et al, Biotechnol Bioeng 69, 607-17 (2000)). However, under such culture conditions currently used widely, it is difficult to remove feeder cells without fail when analyzing the differentiation of ES cells, and therefore, the effect caused by the addition of differentiation-inducing factors-cannot be analyzed correctly. Further, though ES cell lines that can be cultured without feeder cells are known, for instance, ES-D3, one of mouse ES cell lines, tends to differentiate spontaneously under the culture conditions without using feeder layer.

In addition, a serum contains fluctuating amounts of components of activin and fibroblast growth factors or unknown differentiation-inducing factors. When analyzing cell growth and differentiation of ES cells after adding various substances exogenously, these components may have an effect on results of analysis. Further, there is a risk of infection with viruses, prions and unknown factors in the use of serum, and its application to regenerative medicine involves a risk. Furthermore, though serum-free culture conditions of ES cells have been reported, ES cells may differentiate into nerves, etc., after several passages and cannot always maintain their undifferentiated state.

DISCLOSURE OF THE INVENTION

The object of the present invention is to provide a medium for serum-free culture capable of culturing ES cells for a long period while maintaining their undifferentiated state (pluripotency) without using feeder cells, and a basal medium for preparing the medium thus described.

The present inventors have found that with the use of a medium having particular composition, it becomes possible to culture ES cells while maintaining their undifferentiated state without using feeder cells and sera. In other words, the present invention provides a basal medium for preparing a medium for culturing ES cells, which has composition shown by the following Table I.

TABLE I

| Components | Concentration (mg/L) |
| --- | --- |
| L-alanine | 1.78~2.67 |
| L-arginine | 40~60 |
| L-arginine HCl | 75.8~113.7 |
| L-asparagine H$_2$O | 13.002~19.503 |
| -L-Asparatic acid | 6.66~9.99 |
| L-cysteine HCl•H$_2$O | 7.024~10.536 |
| L-cystine 2HCl | 38.058~57.087 |
| L-glutamic acid | 6.94~10.41 |
| L-glutamine | 439.72~659.58 |
| Glycine | 15.5~23.25 |
| L-histidine | 3~30 |
| L-hydroxyproline | 4~6 |

TABLE I-continued

| Components | Concentration (mg/L) |
| --- | --- |
| L-isoleucine | 52.748~79.122 |
| L-leucine | 54.58~81.87 |
| L-lysine HCl | 73.74~110.61 |
| L-methionine | 15.896~23.844 |
| L-phenylalanine | 30.392~45.588 |
| L-proline | 10.9~16.35 |
| L-serine | 24.9~37.35 |
| L-threonine | 44.42~66.63 |
| L-tryptophan | 7.808~11.712 |
| L-tyrosine | 33.888~50.832 |
| L-valine | 43.86~65.79 |
| Glutathione | 0.2~0.3 |
| Para-aminobenzoic acid | 0.2~0.3 |
| Biotin | 0.04148~0.06222 |
| Calcium pantothenate | 1.746~2.619 |
| Choline chloride | 4.992~7.488 |
| Folic acid | 2.06~3.09 |
| Inositol | 13.48~20.22 |
| Niacinamide | 1.8074~2.7111 |
| Pyridoxal HCl | 1.6~2.4 |
| Pyridoxine HCl | 0.2124~0.3186 |
| Riboflavin | 0.2076~0.3114 |
| Thiamine HCl | 1.868~2.802 |
| Vitamin B$_{12}$ | 0.273~0.4095 |
| Hypoxanthine | 0.816~1.224 |
| Linoleic acid | 0.0168~0.0252 |
| Lipoic acid (thioctic acid) | 0.042~0.063 |
| Putrecine dihydrochloride | 0.0322~0.0483 |
| Thymidine | 0.146~0.219 |
| Sodium chloride | 5279.8~7919.7 |
| Potassium chloride | 284.72~427.08 |
| Calcium chloride (anhydrous) | 86.644~129.966 |
| Calcium nitrate 4H$_2$O | 20~30 |
| Magnesium chloride (anhydrous) | 11.444~17.166 |
| Magnesium sulfate (anhydrous) | 48.844~73.266 |
| Sodium dihydrogen phosphate (anhydrous) | 43.48~65.22 |
| Disodium monohydrogen phosphate (anhydrous) | 188.408~282.612 |
| Glucose (anhydrous) | 1860.4~2790.6 |
| Sodium pyruvate | 0.001~220 |
| Ferric nitrate 9H$_2$O | 0.04~0.06 |
| Copper sulfate 5H$_2$O | 0.0005~0.00075 |
| Ferrous sulfate 7H$_2$O | 0.1668~0.2502 |
| Zinc sulfate 7H$_2$O | 0.1728~0.2592 |
| Sodium selenite | 0.000692~0.00348 |
| Phenol red | 5.248~7.872 |

In another aspect, the present invention provides a basal medium for preparing a medium for culturing ES cells, which has composition shown by the following Table II.

TABLE II

| Components | Concentration (mg/L) |
| --- | --- |
| L-alanine | 1.78~2.67 |
| L-arginine | 40~60 |
| L-arginine HCl | 75.8~113.7 |
| L-asparagine H$_2$O | 13.002~19.503 |
| L-Asparatic acid | 6.66~9.99 |
| L-cysteine HCl•H$_2$O | 7.024~10.536 |
| L-cystine 2HCl | 38.058~57.087 |
| L-glutamic acid | 6.94~10.41 |
| L-glutamine | 439.72~659.58 |
| Glycine | 15.5~23.25 |
| L-histidine | 3~30 |
| L-hydroxyproline | 4~6 |
| L-isoleucine | 52.748~79.122 |
| L-leucine | 54.58~81.87 |
| L-lysine HCl | 73.74~110.61 |
| L-methionine | 15.896~23.844 |
| L-phenylalanine | 30.392~45.588 |

TABLE II-continued

| Components | Concentration (mg/L) |
|---|---|
| L-proline | 10.9~16.35 |
| L-serine | 24.9~37.35 |
| L-threonine | 44.42~66.63 |
| L-tryptophan | 7.808~11.712 |
| L-tyrosine | 33.888~50.832 |
| L-valine | 43.86~65.79 |
| Glutathione | 0.2~0.3 |
| Para-aminobenzoic acid | 0.2~0.3 |
| Biotin | 0.04148~0.06222 |
| Calcium pantothenate | 1.746~2.619 |
| Choline chloride | 4.992~7.488 |
| Folic acid | 2.06~3.09 |
| Inositol | 13.48~20.22 |
| Niacinamide | 1.8074~2.7111 |
| Pyridoxal HCl | 1.6~2.4 |
| Pyridoxine HCl | 0.2124~0.3186 |
| Riboflavin | 0.2076~0.3114 |
| Thiamine HCl | 1.868~2.802 |
| Vitamin $B_{12}$ | 0.273~0.4095 |
| Hypoxanthine | 0.816~1.224 |
| Linoleic acid | 0.0168~0.0252 |
| Lipoic acid (thioctic acid) | 0.042~0.063 |
| Putrecine dihydrochloride | 0.0322~0.0483 |
| Thymidine | 0.146~0.219 |
| Sodium chloride | 5279.8~7919.7 |
| Potassium chloride | 284.72~427.08 |
| Calcium chloride (anhydrous) | 86.644~129.966 |
| Calcium nitrate $4H_2O$ | 20~30 |
| Magnesium chloride (anhydrous) | 11.444~17.166 |
| Magnesium sulfate (anhydrous) | 48.844~73.266 |
| Sodium dihydrogen phosphate (anhydrous) | 43.48~65.22 |
| Disodium monohydrogen phosphate (anhydrous) | 188.408~282.612 |
| Glucose (anhydrous) | 1860.4~2790.6 |
| Sodium pyruvate | 0.001~220 |
| Ferric nitrate $9H_2O$ | 0.04~0.06 |
| Copper sulfate $5H_2O$ | 0.0005~0.00075 |
| Ferrous sulfate $7H_2O$ | 0.1668~0.2502 |
| Zinc sulfate $7H_2O$ | 0.1728~0.2592 |
| Phenol red | 5.248~7.872 |

In yet another aspect, the present invention provides a basal medium for preparing a medium for culturing ES cells, which has composition shown by the following Table III.

TABLE III

| Components | Concentration (mg/L) |
|---|---|
| L-alanine | 1.78~2.67 |
| L-arginine | 40~60 |
| L-arginine HCl | 75.8~113.7 |
| L-asparagine $H_2O$ | 13.002~19.503 |
| L-Asparatic acid | 6.66~9.99 |
| L-cysteine HCl•$H_2O$ | 7.024~10.536 |
| L-cystine 2HCl | 38.058~57.087 |
| L-glutamic acid | 6.94~10.41 |
| L-glutamine | 439.72~659.58 |
| Glycine | 15.5~23.25 |
| L-histidine | 3~30 |
| L-hydroxyproline | 4~6 |
| L-isoleucine | 52.748~79.122 |
| L-leucine | 54.58~81.87 |
| L-lysine HCl | 73.74~110.61 |
| L-methionine | 15.896~23.844 |
| L-phenylalanine | 30.392~45.588 |
| L-proline | 10.9~16.35 |
| L-serine | 24.9~37.35 |
| L-threonine | 44.42~66.63 |
| L-tryptophan | 7.808~11.712 |
| L-tyrosine | 33.888~50.832 |
| L-valine | 43.86~65.79 |

TABLE III-continued

| Components | Concentration (mg/L) |
|---|---|
| Glutathione | 0.2~0.3 |
| Para-aminobenzoic acid | 0.2~0.3 |
| Biotin | 0.04148~0.06222 |
| Calcium pantothenate | 1.746~2.619 |
| Choline chloride | 4.992~7.488 |
| Folic acid | 2.06~3.09 |
| Inositol | 13.48~20.22 |
| Niacinamide | 1.8074~2.7111 |
| Pyridoxal HCl | 1.6~2.4 |
| Pyridoxine HCl | 0.2124~0.3186 |
| Riboflavin | 0.2076~0.3114 |
| Thiamine HCl | 1.868~2.802 |
| Vitamin $B_{12}$ | 0.273~0.4095 |
| Hypoxanthine | 0.816~1.224 |
| Linoleic acid | 0.0168~0.0252 |
| Lipoic acid (thioctic acid) | 0.042~0.063 |
| Putrecine dihydrochloride | 0.0322~0.0483 |
| Thymidine | 0.146~0.219 |
| Sodium chloride | 5279.8~7919.7 |
| Potassium chloride | 284.72~427.08 |
| Calcium chloride (anhydrous) | 86.644~129.966 |
| Calcium nitrate $4H_2O$ | 20~30 |
| Magnesium chloride (anhydrous) | 11.444~17.166 |
| Magnesium sulfate (anhydrous) | 48.844~73.266 |
| Sodium dihydrogen phosphate (anhydrous) | 43.48~65.22 |
| Disodium monohydrogen phosphate (anhydrous) | 188.408~282.612 |
| Glucose (anhydrous) | 1860.4~2790.6 |
| Ferric nitrate $9H_2O$ | 0.04~0.06 |
| Copper sulfate $5H_2O$ | 0.0005~0.00075 |
| Ferrous sulfate $7H_2O$ | 0.1668~0.2502 |
| Zinc sulfate $7H_2O$ | 0.1728~0.2592 |
| Phenol red | 5.248~7.872 |

In another aspect, the basal medium of the present invention further comprises 2.5 to 4.5 g/L HEPES, and $NaHCO_3$ in an amount required for an adjustment to desired pH.

In yet another aspect, the present invention provides a method for culturing ES cells using the medium for culturing ES cells of the present invention.

BEST MODE OF CARRYING OUT THE INVENTION

Figure 1:
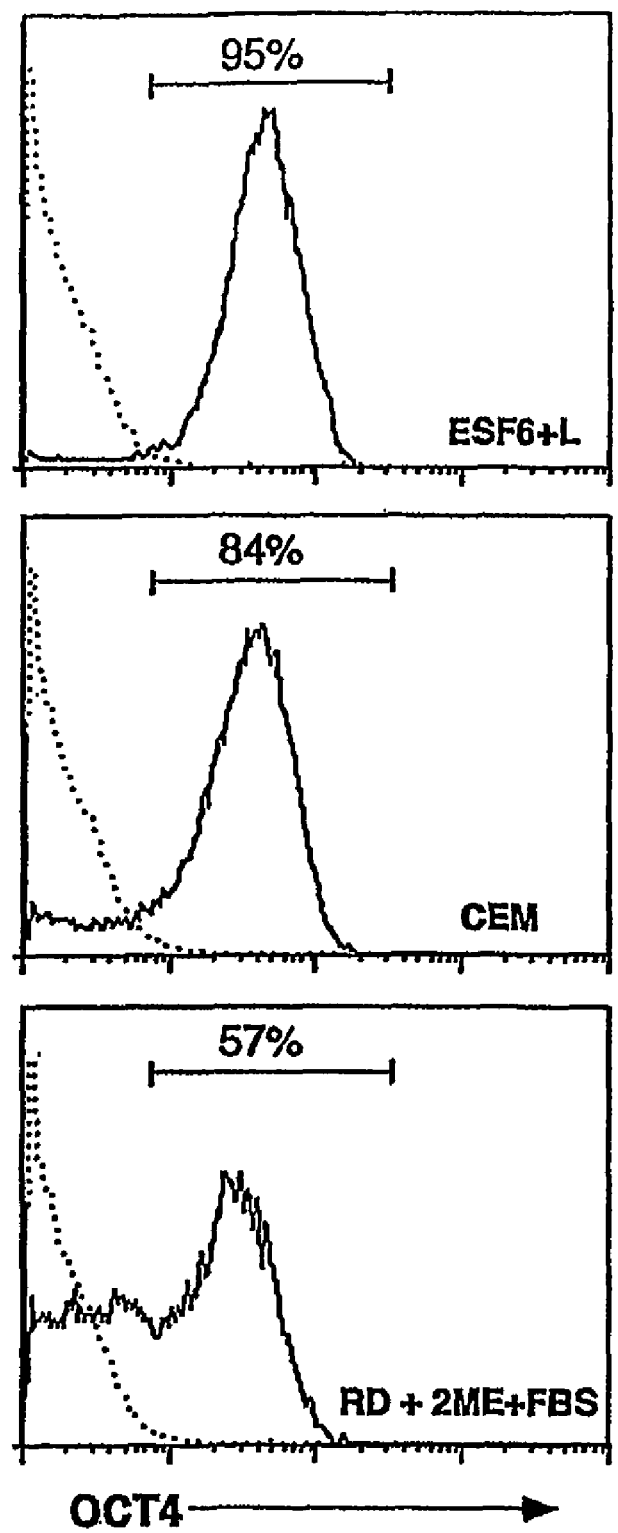
FIG. 1 shows the flow cytometric analysis of Oct3/4 expression in ES-D3 cells cultured in various media.

The present invention provides a basal medium for preparing a serum-free synthetic medium for growing undifferentiated mouse ES cells in the absence of feeder cells. The basal medium of the present invention (hereinafter referred to as "ESF medium") can be easily produced by: adding each component shown in the above-mentioned tables to water until each component reaches a prescribed concentration; further adding 2.5 to 4.5 g/L HEPES, and $NaHCO_3$ in an amount required for an adjustment to desired pH; and then conducting sterilization by using a method well known in the art. Basic components such as basic amino acids may be added in a form of free bases, or of salts such as HCl salt. Six factors (6F; insulin, transferrin, 2-ME, 2-ethanolamine, sodium selenite, oleic acid which has formed a complex with fatty acid-free bovine serum albumin) and LIF (leukemia inhibitory factor) are supplemented to the basal medium of the present invention to produce the medium for culturing ES cells of the present invention (hereinafter referred to as "SF7 medium"). These 6 factors and LIF are commercially available. With the use of the ESF7 medium, ES cells can be maintained under serum-free conditions in a type I collagen-coated flask. Alternatively, the medium for culturing ES cells of the present invention may be produced by appropriately mixing commercially available media. For example, the medium can be conveniently produced by mixing commercially available RPMI, DMEM and F12 at the ratio of 1:2:1, and by adding HEPES, NaHCO$_3$, pyruvic acid, sodium selenite. In this case, however, it is more preferable to add a total of 23.165 g/L of L-histidine instead of L-histidine HCl·H$_2$O before use.

As shown in the Examples to be hereinafter described, when mouse ES cells were cultured in the ESF7 medium in accordance with the present invention, the ES cells maintained their undifferentiated phenotype as shown by the expression of a transcription factor Oct3/4, a stem cell marker SSEA-1, and alkaline phosphatase. In addition, when a bone morphogenetic factor 4 (BMP4) was added to the undifferentiated cells thus maintained, differentiation into epithelial-like cells was induced. Further, when activin A was added, differentiation of ES cells into fibroblastic-like cells and spiny cells was promoted. In other words, the ES cells cultured in the ESF7 medium in accordance with the present invention maintained an ability to differentiate into particular cells in response to the stimuli of differentiation-inducing factors.

With regard to the basal medium of the present invention, the concentration of L-alanine is 1.78 mg/L to 2.67 mg/L, preferably, 2.0025 mg/L to 2.4475 mg/L, more preferably, 2.11375 mg/L to 2.33625 mg/L. The concentration of L-arginine is 40 mg/L to 60 mg/L, preferably, 45 mg/L to 55 mg/L, more preferably, 47.5 mg/L to 52.5 mg/L. The concentration of L-arginine HCl is 75.8 mg/L to 113.7 mg/L, preferably, 85.275 mg/L to 104.225 mg/L, more preferably, 90.0125 mg/L to 99.4875 mg/L. The concentration of L-asparagine H$_2$O is 13.002 mg/L to 19.503 mg/L, preferably, 14.62725 mg/L to 17.87775 mg/L, more preferably, 15.43988 mg/L to 17.06513 mg/L. The concentration of L-aspartate is 6.66 mg/L to 9.99 mg/L, preferably, 7.4925 mg/L to 9.1575 mg/L, more preferably, 7.90875 mg/L to 8.74125 mg/L. The concentration of L-cysteine HCl ,H$_2$O is 7.024 mg/L to 10.536 mg/L, preferably, 7.902 mg/L to 9.658 mg/L, more preferably, 8.341 mg/L to 9.219 mg/L. The concentration of L-cystine 2HCl is 38.058 mg/L to 57.087 mg/L, preferably, 42.81525 mg/L to 52.32975 mg/L, more preferably, 45.19388 mg/L to 49.95113 mg/L. The concentration of L-glutamate is 6.94 mg/L to 10.41 mg/L, preferably, 7.8075 mg/L to 9.5425 mg/L, more preferably, 8.24125 mg/L to 9.10875 mg/L. The concentration of L-glutamine is 439.72 mg/L to 659.58 mg/L, preferably, 494.685 mg/L to 604.615 mg/L, more preferably, 522.1675 mg/L to 577.1325 mg/L. The concentration of glycine is 15.5 mg/L to 23.25 mg/L, preferably, 17.4375 mg/L to 21.3125 mg/L, more preferably, 18.40625 mg/L to 20.34375 mg/L. The concentration of L-histidine is 3 mg/L to 30 mg/L, preferably, 20.8485 mg/L to 25.4815 mg/L, more preferably, 22.00675 mg/L to 24.32325 mg/L. The concentration of L-hydroxyproline is 4 mg/L to 6 mg/L, preferably, 4.5 mg/L to 5.5 mg/L, more preferably, 4.75 mg/L to 5.25 mg/L. The concentration of L-isoleucine is 52.748 mg/L to 79.122 mg/L, preferably, 59.3415 mg/L to 72.5285 mg/L, more preferably, 62.63825 mg/L to 69.23175 mg/L. The concentration of L-leucine is 54.58 mg/L to 81.87 mg/L, preferably, 61.4025 mg/L to 75.0475 mg/L, more preferably, 64.81375 mg/L to 71.63625 mg/L. The concentration of L-lysine HCl is 73.74 mg/L to 110.61 mg/L, preferably, 82.9575 mg/L to 101.3925 mg/L, more preferably, 87.56625 mg/L to 96.78375 mg/L. The concentration of L-methionine is 15.896 mg/L to 23.844 mg/L, preferably, 17.883 mg/L to 21.857 mg/L, more preferably, 18.8765 mg/L to 20.8635 mg/L. The concentration of L-phenylalanine is 30.392 mg/L to 45.588 mg/L, preferably, 34.191 mg/L to 41.789 mg/L, more preferably, 36.0905 mg/L to 39.8895 mg/L. The concentration of L-proline is 10.9 mg/L to 16.35 mg/L, preferably, 12.2625 mg/L to 14.9875 mg/L, more preferably, 12.94375 mg/L to 14.30625 mg/L. The concentration of L-serine is 24.9 mg/L to 37.35 mg/L, preferably, 28.0125 mg/L to 34.2375 mg/L, more preferably, 29.56875 mg/L to 32.68125 mg/L. The concentration of L-threonine is 44.42 mg/L to 66.63 mg/L, preferably, 49.9725 mg/L to 61.0775 mg/L, more preferably, 52.74875 mg/L to 58.30125 mg/L. The concentration of L-tryptophan is 7.808 mg/L to 11.712 mg/L, preferably, 8.784 mg/L to 10.736 mg/L, more preferably, 9.272 mg/L to 10.248 mg/L. The concentration of L-tyrosine is 33.888 mg/L to 50.832 mg/L, preferably, 38.124 mg/L to 46.596 mg/L, more preferably, 40.242 mg/L to 44.478 mg/L. The concentration of L-valine is 43.86 mg/L to 65.79 mg/L, preferably, 49.3425 mg/L to 60.3075 mg/L, more preferably, 52.08375 mg/L to 57.56625 mg/L.

The concentration of glutathione is 0.2 mg/L to 0.3 mg/L, preferably, 0.225 mg/L to 0.275 mg/L, more preferably, 0.2375 mg/L to 0.2625 mg/L. The concentration of para-aminobenzoic acid is 0.2 mg/L to 0.3 mg/L, preferably, 0.225 mg/L to 0.275 mg/L, more preferably, 0.2375 mg/L to 0.2625 mg/L. The concentration of biotin is 0.04148 mg/L to 0.06222 mg/L, preferably, 0.046665 mg/L to 0.057035 mg/L, more preferably, 0.049258 mg/L to 0.054443 mg/L. The concentration of calcium pantothenate is 1.746 mg/L to 2.619 mg/L, preferably, 1.96425 mg/L to 2.40075 mg/L, more preferably, 2.073375 mg/L to 2.291625 mg/L. The concentration of choline chloride is 4.992 mg/L to 7.488 mg/L, preferably, 5.616 mg/L to 6.864 mg/L, more preferably, 5.928 mg/L to 6.552 mg/L. The concentration of folic acid is 2.06 mg/L to 3.09 mg/L, preferably, 2.3175 mg/L to 2.8325 mg/L, more preferably, 2.44625 mg/L to 2.70375 mg/L. The concentration of inositol is 13.48 mg/L to 20.22 mg/L, preferably, 15.165 mg/L to 18.535 mg/L, more preferably, 16.0075 mg/L to 17.6925 mg/L. The concentration of niacinamide is 1.8074 mg/L to 2.7111 mg/L, preferably, 2.033325 mg/L to 2.485175 mg/L, more preferably, 2.146288 mg/L to 2.372213 mg/L. The concentration of pyridoxal HCl is 1.6 mg/L to 2.4 mg/L, preferably, 1.8 mg/L to 2.2 mg/L, more preferably, 1.9 mg/L to 2.1 mg/L. The concentration of pyridoxine HCl is 0.2124 mg/L to 0.3186 mg/L, preferably, 0.23895 mg/L to 0.29205 mg/L, more preferably, 0.252225 mg/L to 0.278775 mg/L. The concentration of riboflavin is 0.2076 mg/L to 0.3114 mg/L, preferably, 0.23355 mg/L to 0.28545 mg/L, more preferably, 0.246525 mg/L to 0.272475 mg/L. The concentration of thiamine HCl is 1.868 mg/L to 2.802 mg/L, preferably, 2.1015 mg/L to 2.5685 mg/L, more preferably, 2.21825 mg/L to 2.45175 mg/L. The concentration of vitamin B12 is 0.273 mg/L to 0.4095 mg/L, preferably, 0.307125 mg/L to 0.375375 mg/L, more preferably, 0.324188 mg/L to 0.358313 mg/L. The concentration of hypoxanthine is 0.816 mg/L to 1.224 mg/L, preferably, 0.918 mg/L to 1.122 mg/L, more preferably, 0.969 mg/L to 1.071 mg/L. The concentration of linoleic acid is 0.0168 mg/L to 0.0252 mg/L, preferably, 0.0189 mg/L to 0.0231 mg/L, more preferably, 0.01995 mg/L to 0.02205 mg/L. The concentration of lipotic acid (thioctic acid) is 0.042 mg/L to 0.063 mg/L, preferably, 0.04725 mg/L to 0.05775 mg/L, more preferably, 0.049875 mg/L to 0.055125 mg/L. The concentration of Putrecine dihydrochloride is 0.0322 mg/L to 0.0483 mg/L, preferably, 0.036225 mg/L to 0.044275 mg/L, more preferably, 0.038238 mg/L to 0.042263 mg/L. The concentration of thymidine is 0.146 mg/L to 0.219 mg/L, preferably, 0.16425 mg/L to 0.20075 mg/L, more preferably, 0.173375 mg/L to 0.191625 mg/L.

The concentration of sodium chloride is 5279.8 mg/L to 7919.7 mg/L, preferably, 5939.775 mg/L to 7259.725 mg/L, more preferably, 6269.763 mg/L to 6929.738 mg/L. The concentration of potassium chloride is 284.72 mg/L to 427.08 mg/L, preferably, 320.31 mg/L to 391.49 mg/L, more preferably, 338.105 mg/L to 373.695 mg/L. The concentration of calcium chloride (anhydrous) is 86.644 mg/L to 129.966 mg/L, preferably, 97.4745 mg/L to 119.1355 mg/L, more preferably, 102.8898 mg/L to 113.7203 mg/L. The concentration of calcium nitrate $4H_2O$ is 20 mg/L to 30 mg/L, preferably, 22.5 mg/L to 27.5 mg/L, more preferably, 23.75 mg/L to 26.25 mg/L. The concentration of magnesium chloride (anhydrous) is 11.444 mg/L to 17.166 mg/L, preferably, 12.8745 mg/L to 15.7355 mg/L, more preferably, 13.58975 mg/L to 15.02025 mg/L. The concentration of magnesium sulfate (anhydrous) is 48.844 mg/L to 73.266 mg/L, preferably, 54.9495 mg/L to 67.1605 mg/L, more preferably, 58.00225 mg/L to 64.10775 mg/L. The concentration of sodium dihydrogen phosphate (anhydrous) is 43.48 mg/L to 65.22 mg/L, preferably, 48.915 mg/L to 59.785 mg/L, more preferably, 51.6325 mg/L to 57.0675 mg/L. The concentration of disodium monohydrogen phosphate (anhydrous) is 188.408 mg/L to 282.612 mg/L, preferably, 211.959 mg/L to 259.061 g/L, more preferably, 223.7345 mg/L to 247.2855 mg/L. The concentration of glucose (anhydrous) is 1860.4 mg/L to 2790.6 mg/L, preferably, 2092.95 mg/L to 2558.05 mg/L, more preferably, 2209.225 mg/L to 2441.775 mg/L. The concentration of sodium pyruvate is 0.001 mg/L to 220 mg/L, preferably, 50 mg/L to 170 mg/L, more preferably, 100 mg/L to 120 mg/L. Sodium pyruvate is not necessarily contained in the basal medium, it may be added later. The concentration of ferric nitrate $9H_2O$ is 0.04 mg/L to 0.06 mg/L, preferably, 0.045 mg/L to 0.055 mg/L, more preferably, 0.0475 mg/L to 0.0525 mg/L. The concentration of copper sulfate $5H_2O$ is 0.0005 mg/L to 0.00075 mg/L, preferably, 0.000563 mg/L to 0.000688 mg/L, more preferably, 0.000594 mg/L to 0.000656 mg/L. The concentration of ferrous sulfate $7H_2O$ is 0.1668 mg/L to 0.2502 mg/L, preferably, 0.18765 mg/L to 0.22935 mg/L, more preferably, 0.198075 mg/L to 0.218925 mg/L. The concentration of zinc sulfate $7H_2O$ is 0.1728 mg/L to 0.2592 mg/L, preferably, 0.1944 mg/L to 0.2376 mg/L, more preferably, 0.2052 mg/L to 0.2268 mg/L. The concentration of sodium selenite is 0.000692 mg/L to 0.00348 mg/L, preferably, 0.000779 mg/L to 0.00291 mg/L, more preferably, 0.000822 mg/L to 0.00263 mg/L. Sodium selenite is not necessarily contained in the basal medium, it may be added later. The concentration of phenol red is 5.248 mg/L to 7.872 mg/L, preferably, 5.904 mg/L to 7.216 mg/L, more preferably, 6.232 mg/L to 6.888 mg/L.

The concentration of HEPES to be added to the basal medium of the present invention is 2859.6 mg/L to 4289.4 mg/L, preferably, 3217.05 mg/L to 3931.95 mg/L, more preferably, 3395.775 mg/L to 3753.225 mg/L. The concentration of $NaHCO_3$ is 1600 mg/L to 2400 mg/L, preferably, 1800 mg/L to 2200 mg/L, more preferably, 1900 mg/L to 2100 mg/L.

The use of the medium for culturing ES cells of the present invention makes it possible to grow ES cells while maintaining their undifferentiated state without using feeder cells. Consequently, it is possible to examine the effects of various factors on the differentiation of ES cells in a reproducible fashion. In addition, it becomes easier to establish the conditions under which ES cells differentiate into particular cells or organs, and it makes it possible to induce ES cells to differentiate in test tubes (or in vitro) along a previously prescribed pathway. Therefore, the medium for culturing ES cells of the present invention is useful for ES cell studies aimed at application to regenerative medicine.

With regard to the contents of all patents and references expressly quoted herein, all of them are hereby quoted as a part of this description. Further, with regard to the contents described in the description and the drawings of Japanese Patent Application No. 2003-434035, which is an application that forms a basis of the priority claim of the present application, all of them are hereby quoted as a part of this description.

EXAMPLES

The present invention will be described in greater detail with reference to Examples, but these Examples do not limit the scope of the present invention.

Example 1

Preparation of Basal Medium

The basal medium having composition shown by the following table (referred to as "ESF medium") was prepared, and sterilized according to a usual method.

| Components | Concentration (mg/L) |
| --- | --- |
| L-alanine | 2.225 |
| L-arginine | 50 |
| L-arginine HCl | 94.75 |
| L-asparagine $H_2O$ | 16.2525 |
| L-Asparatic acid | 8.325 |
| L-cysteine HCl•$H_2O$ | 8.78 |
| L-cystine 2HCl | 47.5725 |
| L-glutamic acid | 8.675 |
| L-glutamine | 549.65 |
| Glycine | 19.375 |
| L-histidine | 23.165 |
| L-hydroxyproline | 5 |
| L-isoleucine | 65.935 |
| L-leucine | 68.225 |
| L-lysine HCl | 92.175 |
| L-methionine | 19.87 |
| L-phenylalanine | 37.99 |
| L-proline | 13.625 |
| L-serine | 31.125 |
| L-threonine | 55.525 |
| L-tryptophan | 9.76 |
| L-tyrosine | 42.36 |
| L-valine | 54.825 |
| Glutathione | 0.25 |
| Para-aminobenzoic acid | 0.25 |
| Biotin | 0.05185 |
| Calcium pantothenate | 2.1825 |
| Choline chloride | 6.24 |
| Folic acid | 2.575 |
| Inositol | 16.85 |
| Niacinamide | 2.25925 |
| Pyridoxal HCl | 2 |
| Pyridoxine HCl | 0.2655 |
| Riboflavin | 0.2595 |
| Thiamine HCl | 2.335 |
| Vitamin $B_{12}$ | 0.34125 |
| Hypoxanthine | 1.02 |
| Linoleic acid | 0.021 |
| Lipoic acid (thioctic acid) | 0.0525 |
| Putrecine dihydrochloride | 0.04025 |
| Thymidine | 0.1825 |
| Sodium chloride | 6599.75 |
| Potassium chloride | 355.9 |

-continued

| Components | Concentration (mg/L) |
|---|---|
| Calcium chloride (anhydrous) | 108.305 |
| Calcium nitrate 4H$_2$O | 25 |
| Magnesium chloride (anhydrous) | 14.305 |
| Magnesium sulfate (anhydrous) | 61.055 |
| Sodium dihydrogen phosphate (anhydrous) | 54.35 |
| Disodium monohydrogen phosphate (anhydrous) | 235.51 |
| Glucose (anhydrous) | 2325.5 |
| Sodium pyruvate | 110 |
| Ferric nitrate 9H$_2$O | 0.05 |
| Copper sulfate 5H$_2$O | 0.000625 |
| Ferrous sulfate 7H$_2$O | 0.2085 |
| Zinc sulfate 7H$_2$O | 0.216 |
| Sodium selenite | 0.000865 |
| Phenol red | 6.56 |
| HEPES | 3574.5 |
| NaHCO$_3$ | 2000 |

Example 2

Culture and Growth of ES Cells

ES-D3 (ATCC, USA) was used as an ES cell line. Though the cell can be cultured without using feeder cells, it is said that the cell exhibits a tendency to differentiation in such a case. The ES-D3 cells were maintained initially on a 0.1% gelatin-coated plate (Cell & Molecular Technologies, Inc., Phillipburg, N.J.), in Dulbecco's modified Eagle medium supplemented with 15% fetal bovine serum, L-glutamine, 0.1 mM 2-mercaptoethanol, nucleoside, nonessential amino acid, and LIF (complete ES medium; hereinafter referred to as CEM, Cell & Molecular Technologies, Inc., Phillipburg, N.J.). The composition of the CEM medium is shown below.

ES-101-B

Complete ES cell Culture Media

| Part Number | Component |
|---|---|
| SLM-220 | DMEM ES cell qualified, 400 ml |
| TMS-002 | L-Glutamine 8 ml/400 ml media |
| ES-008 | 4 ml nucleosides/400 ml media |
| ES-007 | 4 ml beta-mercaptoethanol/400 ml media |
| TMS-001 | 4 ml NEAA/400 ml media |
| ES-009 | 60 ml FBS/400 ml media |
| LIF | 4 mls LIF/400 ml media |
| TMS-AB2 | 4 ml Pen/Strep/400 ml media |

Base Catalog # SLM-220

| Component | mg/L |
|---|---|
| INORGANIC SALTS | |
| CaCl$_2$ (anhyd.) | 200 |
| Fe(NO$_3$)$_3$—9H$_2$O | 0.1 |
| KCl | 400 |
| MgSO$_4$ (anhyd.) | 97.67 |
| NaCl | 6400 |
| NaHCO$_3$ | 2250 |
| NaH$_2$PO$_4$—H$_2$O | 125 |
| OTHER COMPONENTS | |
| D-Glucose | 4500 |
| Phenol Red | 15 |
| HEPES | — |
| Sodium Pyruvate | — |
| VITAMINS | |
| D-Ca pantothenate | 4 |
| Chlorine Chloride | 4 |
| Folic Acid | 4 |
| I-Inositol | 7.2 |
| Niacinamide | 4 |
| Pyridoxal-HCl | 4 |
| Pyridoxine-HCl | — |
| Riboflavin | 0.4 |
| Thiamine-HCl | 4 |

Working pH range 7.0~7.4

| Component | mg/L |
|---|---|
| AMINO ACIDS | |
| L-Arginine-HCl | 84 |
| L-Cystine | — |
| L-Cystine-2HCl | 63 |
| L-Glutamine | — |
| Glycine | 30 |
| L-Histidine-HCl—H$_2$O | 42 |
| L-Isoleucine | 105 |
| L-Leucine | 105 |
| L-Lysine-HCl | 146 |
| L-Methionine | 30 |
| L-Phenylalanine | 66 |
| L-Serine | 42 |
| L-Threonine | 95 |
| L-Tryptophan | 16 |
| L-Tyrosine | — |
| L-Tyrosine-2Na—2H$_2$O | 104 |
| L-Valine | 94 |

Base Catalog # ES-008

| Component | g/L |
|---|---|
| Cytidine | 0.73 |
| Guanosine | 0.85 |
| Uridine | 0.73 |
| Adenosine | 0.8 |
| Thymidine | 0.24 |

Into a 75 cm$^2$ Corning plastic flask, 10 ml of 0.15 mg/ml Type I collagen solution was poured, and treated for 12 hours while protecting it from drying, and the solution was removed by suction just before seeding cells. A serum-free medium (ESF7 medium) was prepared by adding 6 factors (10 μg/ml bovine insulin, 5 μg/ml human transferrin, 10 μM 2-mercaptoethanol, 10 μM 2-aminoethanol, 10 nM sodium selenite, 4 μg/ml oleic acid which has formed a complex with fatty acid-free bovine serum albumin) and 300 units/ml LIF (ESGRO®, Chemicon International Inc.) to ESF medium. At the passage of the cells, the following treatments were conducted: washing the cells with Dulbecco's phosphate buffer solution; treating the cells with 0.001% trypsin/0.01% EDTA for 10 to 30 seconds; dispersing the cells by pipetting; neutralizing trypsin with 0.1% trypsin inhibitor dissolved in MCDB 153 solution; collecting the cells in ESF medium and conducting centrifugation; dispersing the cells in ESF medium and then conducting centrifugation again; and dispersing the cells in ESF7 medium. When ES-D3 cells were seeded onto ESF7 medium in a collagen-coated flask at a density of 5–7×10$^3$ cells/ml and cultured for several days, a small cell population showing weak adhesiveness and ill-defined borders, and being positive to alkaline phosphatase activity, formed a colony and proliferated.

The determination of undifferentiated phenotypes was conducted as follows. In order to detect alkaline phosphatase activity of the cells, the cells were fixed with 4.5 mM citric acid, 2.25 mM sodium citrate, 3 mM sodium chloride, 65% methanol and 4% paraformaldehyde for 5 minutes, and then washed. Subsequently, alkaline phosphatase was visualized by using FastRed substrate kit (Nichirei Co., Tokyo, Japan) according to the manufacturer's protocol.

For the detection of Oct3/4 protein expression, the cells were fixed with 4% paraformaldehyde (PFA) in PBS at 4° C. for 16 hours. Before incubating with antibodies, the cells were treated with 0.002% trypsin at room temperature for 5 minutes to increase permeability of the cells, and endogenous peroxidase activity was blocked by incubating sections with 3% $H_2O_2$ in methanol for 30 minutes. The sections were immunostained with mouse anti-Oct3/4 (Transduction Laboratories, Lexington, Ky.), and visualized with peroxidase-conjugated SimpleStain MAXPO® goat anti-mouse IgG (NICHIREI Corporation, Tokyo, Japan) and 3-amino-9-ethylcarbazole.

In order to conduct a flow cytometric analysis of Oct3/4 expression, $3 \times 10^5$ ES cells were seeded in ESF7, and in RD+2ME+FBS, on a type I collagen-coated 90 mm plastic plate, and in CEM on a gelatin-coated plastic plate. On day 6 of culture, the cells were trypsinized with trypsin/EDTA in PBS, and subsequently fixed with 1% paraformaldehyde in 0.1 M phosphate buffer solution (pH 7.4) for 1 hour. The cells were treated with 1% saponin (Sigma) in PBS at room temperature for 10 minutes to increase their permeability, and then suspended in 1 ml of 10% goat serum (Nichirei) for 30 minutes, followed by centrifugation, and incubated with anti-Oct3/4 mouse antibody (Transduction Laboratories, Lexington, Ky.) for 1 hour. The cells were washed 3 times with PBS containing 1% goat serum, and then reacted with fluorescein (FITC)-conjugated goat anti-mouse IgG antibody (Immunotech, France) for 30 minutes. The cells were washed 3 times with PBS containing 1% goat serum. Resuspended cells were analyzed with EpicsAltra (Beckman Coulter Co., Miami, Fla.).

The phenotype of ES-D3 cells which had been cultured for 5 days in the ESF7 medium in the collagen-coated flask, and that of ES-D3 cells which had been cultured for 5 days in the CEM in the 0.1% gelatin-coated flask were compared by observing their cytomorphology. Most of ES cells grown in the ESF7 medium remained undifferentiated. However, the culture in the CEM contained a mixture of undifferentiated cells, fibroblast-like cells, epithelial-like cells, and neural-like cells. The undifferentiated state of ES cells is usually confirmed by determining the ratio of cells stained with the antibodies to stem cell marker/Oct3/4. By immunohistochemical staining, most of ES-D3 cells in the ESF7 medium expressed Oct3/4 protein, but in the CEM, less cells expressed Oct3/4. When examined with flow cytometry, 95% or more of the cells in the ESF7 medium expressed Oct3/4 protein, but in the CEM, less than 85% of the cells expressed Oct3/4 (FIG. 1). In the RD nutrient medium supplemented with 15% FBS and 2-mercaptoethanol, the percentage of Oct3/4-positive cells was less than 60%.

Example 3

Effect of LIF Concentration

The effect of LIF on the proliferation of ES-D3 cells was examined. The ES-D3 cells were seeded at $5 \times 10^3$ cells/well in ESF6 (ESF+6 factors), and in RD+6F, on a type I collagen-coated 24-well plate, and in DMEM+15% FBS+2-mercaptoethanol on a gelatin-coated 24-well plate. To each well, LIF was added at 0, 1, 10, 100, 500, 1000 units/ml. After culturing 6 days, the cells were counted with a Coulter counter.

Figure 2:
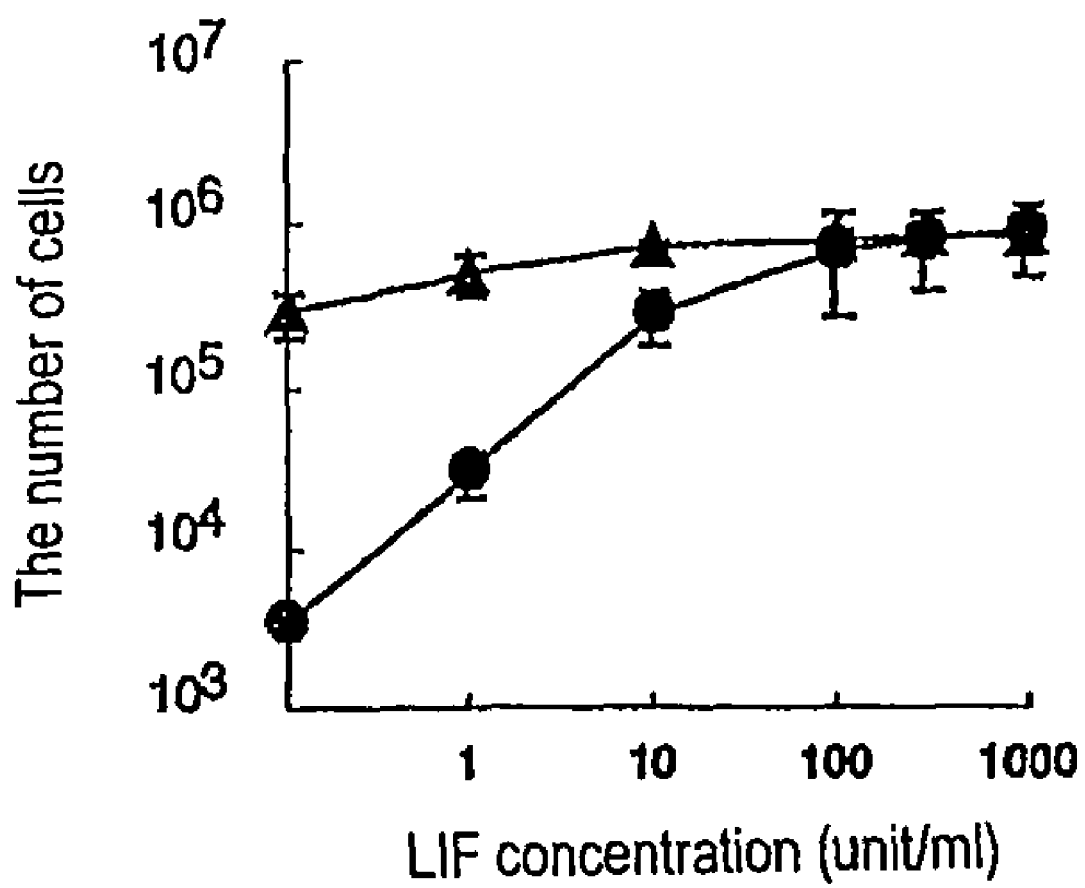
FIG. 2 shows the effect of LIF concentration on the growth of ES-D3 cells.

It is known that LIF maintains a self-replicating ability and an undifferentiated state of ES cells but it has no effect on cell proliferation. However, as shown in FIG. 2, LIF obviously stimulated the proliferation of ES cells in a concentration-dependent manner in the ESF6 medium (closed circle). On the other hand, LIF had little effect on cell proliferation in DMEM (closed triangle) supplemented with 15% FBS and 2-mercaptoethanol. In other words, the use of the chemosynthetic serum-free ESF6 medium of the present invention has made it possible to distinguish a previously unknown activity of LIF to mouse ES cells.

Even in the case where LIF was removed from the ESF7 medium, spontaneous differentiation of ES-D3 cells was not observed. When FBS was added to the medium in the absence of LIF, the ES-D3 cells differentiated into fibroblast-like cells, epithelial-like cells, and neural-like cells. This indicates that the ES-D3 cells maintained their undifferentiated state in the ESF6 medium.

Example 4

ES Cell Proliferation

Figure 3:
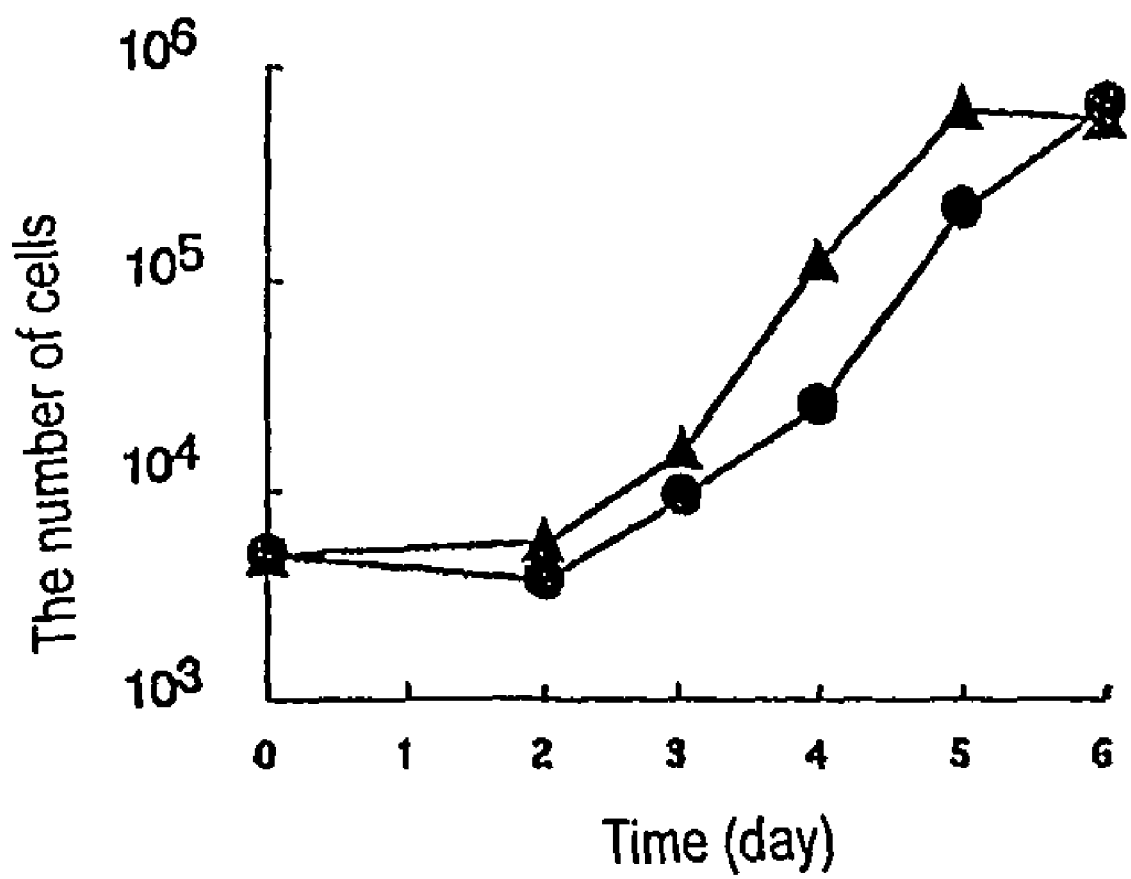
FIG. 3 shows the proliferation of ES-D3 cells cultured in ESF7 medium and CEM medium.

The ES-D3 cells were seeded at $1 \times 10^4$ cells/well in ESF7 on a type I collagen-coated 24-well plate (Falcon), and in CEM on a gelatin-coated 24-well plate, to compare their cell proliferation (FIG. 3). The ES-D3 cells proliferated well in the CEM (closed triangle; Td=9 hours). Though the ES-D3 cells in the ESF7 medium proliferated more slowly than those in the CEM (closed circle; Td=11.8 hours), there was little difference in the cell density between the media on day 6 of culture. Even when the ES-D3 cells were continuously cultured for 1 year or longer in the ESF7 medium, the cells did not change their morphology and kept expressing alkaline phosphatase activity, Oct3/4 and SSEA-1.

Example 5

Culture of ES 129Sv Cells

The effect of ESF7 medium on the culture of ES 129Sv cells was examined. Frozen 129/SV ES cells at the $10^{th}$ passage (Cell & Molecular Technologies, Inc., Phillipburg, N.J.) were purchased, and maintained on feeder cells in CME. 129/SV ES cells were pipetted in PBS containing type I collagenase, and inoculated into ESF7 medium (2000 units of LIF/ml), without feeder cells, in a collagen-coated flask. The ES 129Sv cells proliferated slowly, and there emerged neural-like cells as well. However, from the measurement of immunohistological expression using alkaline phosphatase activity and Oct3/4 antibody, it has been revealed that the ES 129Sv cells had proliferated in the ESF7 medium without differentiating. In other words, it has been shown that with the use of the medium for culturing ES cells of the present invention, ES cells, which usually proliferate on feeder cells, also proliferate without feeder cells. During passage of cells, however, the cells were dispersed with the use of 0.3 unit/ml of type IA-S collagenase instead of trypsin EDTA.

Example 6

Induction of Differentiation by BMP4, activin A and FGF-2

ES-D3 cells were inoculated into ESF7 on a laminin-coated plastic plate, and cultured for 2 days. Next, the medium was replaced with RD+5F medium (RD supplemented with 5 factors). RD medium is a basal medium for serum-free synthetic media generally used for non-ES cell type. For adding BMP4, fatty acid-free BSA was supplemented to the RD+5F medium.

When activin A was added to RD+5F, the ES-D3 cells were induced to differentiate into fibroblast-like cells. By the addition of BMP4 to RD+5F supplemented with fatty acid-free BSA (bovine serum albumin), the ES cells differentiated into epithelial-like cells. These results indicate that ES cells can be induced to differentiate along a specific pathway in response to growth factors. ES-D3 cells were inoculated into ESF7 on a laminin-coated plastic plate, and cultured for 2 days. Next, the medium was replaced with ESF5. For adding BMP4 fatty acid-free BSA (bovine serum albumin) was supplemented to the ESF5. Alternatively, ES-D3 cells were inoculated onto a laminin-coated plastic plate with the use of ESF5 as a medium, BMP4 and fatty acid-free BSA were added to the medium, and the cells were cultured. The medium was replaced every other day. Alternatively, ES-D3 cells were cultured as follows: ES-D3 cells were inoculated onto a laminin-coated plastic plate with the use of ESF5 as a medium; FGF-2 and heparin, or, FGF-2, heparin and NGF, or, FGF-2, heparin and PDGF-AA were added to the medium; after culturing the cells for 1 day, only growth factors were added to each medium; after further culturing the cells for 2 days, the medium was replaced with ESF5; and the cells were cultured. The medium was replaced every other day.

When activin A was added to ESF5, the ES-D3 cells were induced to differentiate into fibroblast-like cells. By the addition of BMP4 to ESF5 supplemented with fatty acid-free BSA (bovine serum albumin), the ES cells differentiated into epithelial-like cells. When FGF-2 and heparin, or, in addition to FGF-2 and heparin, NGF or PDGF-AA were added to ESF5, the cells differentiated into neural-like cells. These results indicate that ES cells can be induced to differentiate along a specific pathway in response to growth factors.

Example 7

Culture of ES C57/BL6J ES Cells

The effect of ESF7 medium on the culture of C57/BL6J ES cells was examined. Frozen C57/BL6J ES cells at the 10$^{th}$ passage (Cell & Molecular Technologies, Inc., Phillipburg, N.J.) were purchased, and maintained on feeder cells in CME. C57/BL6J ES cells were pipetted in PBS only, or in PBS containing type I collagenase, and inoculated into ESF7 medium (3000 units of LIF/ml), without feeder cells, in a collagen-coated flask. The C57/BL6J ES cells formed a colony in an undifferentiated state, and proliferated slowly. In other words, it has been shown that with the use of the medium for culturing ES cells of the present invention, ES cells, which usually proliferate on feeder cells, also proliferate without feeder cells.

INDUSTRIAL APPLICABILITY

With the use of the medium according to the present invention, it becomes possible to conduct serum-free culture of ES cells for a long period while maintaining their undifferentiated state without using feeder cells, and therefore, it is useful for the growth and differentiation induction of ES cells.

The invention claimed is:

1. A medium for culturing embryonic stem (ES) cells comprising: (a) insulin, transferrin, 2-mercaptoethanol, 2-ethanolamine, sodium selenite, oleic acid which has formed a complex with fatty acid-free bovine serum albumin, and LIF (leukemia inhibitory factor; and (b) the basal medium comprising the composition shown by the following Table III.

TABLE III

| Components | Concentration (mg/L) |
| --- | --- |
| L-alanine | 1.78~2.67 |
| L-arginine | 40~60 |
| L-arginine HCl | 75.8~113.7 |
| L-asparagine H$_2$O | 13.002~19.503 |
| L-Aspartic acid | 6.66~9.99 |
| L-cysteine HCl•H$_2$O | 7.024~10.536 |
| L-cystine 2HCl | 38.058~57.087 |
| L-glutamic acid | 6.94~10.41 |
| L-glutamine | 439.72~659.58 |
| Glycine | 15.5~23.25 |
| L-histidine | 3~30 |
| L-hydroxyproline | 4~6 |
| L-isoleucine | 52.748~79.122 |
| L-leucine | 54.58~81.87 |
| L-lysine HCl | 73.74~110.61 |
| L-methionine | 15.896~23.844 |
| L-phenylalanine | 30.392~45.588 |
| L-proline | 10.9~16.35 |
| L-serine | 24.9~37.35 |
| L-threonine | 44.42~66.63 |
| L-tryptophan | 7.808~11.712 |
| L-tyrosine | 33.888~50.832 |
| L-valine | 43.86~65.79 |
| Glutathione | 0.2~0.3 |
| Para-aminobenzoic acid | 0.2~0.3 |
| Biotin | 0.04148~0.06222 |
| Calcium pantothenate | 1.746~2.619 |
| Choline chloride | 4.992~7.488 |
| Folic acid | 2.06~3.09 |
| Inositol | 13.48~20.22 |
| Niacinamide | 1.8074~2.7111 |
| Pyridoxal HCl | 1.6~2.4 |
| Pyridoxine HCl | 0.2124~0.3186 |
| Riboflavin | 0.2076~0.3114 |
| Thiamine HCl | 1.868~2.802 |
| Vitamin B$_{12}$ | 0.273~0.4095 |
| Hypoxanthine | 0.816~1.224 |
| Linoleic acid | 0.0168~0.0252 |
| Lipoic acid (thioctic acid) | 0.042~0.063 |
| Putrecine dihydrochloride | 0.0322~0.0483 |
| Thymidine | 0.146~0.219 |
| Sodium chloride | 5279.8~7919.7 |
| Potassium chloride | 284.72~427.08 |
| Calcium chloride (anhydrous) | 86.644~129.966 |
| Calcium nitrate 4H$_2$O | 20~30 |
| Magnesium chloride (anhydrous) | 11.444~17.166 |
| Magnesium sulfate (anhydrous) | 48.844~73.266 |
| Sodium dihydrogen phosphate (anhydrous) | 43.48~65.22 |
| Disodium monohydrogen phosphate (anhydrous) | 188.408~282.612 |
| Glucose (anhydrous) | 1860.4~2790.6 |
| Ferric nitrate 9H$_2$O | 0.04~0.06 |
| Copper sulfate 5H$_2$O | 0.0005~0.00075 |
| Ferrous sulfate 7H$_2$O | 0.1668~0.2502 |
| Zinc sulfate 7H$_2$O | 0.1728~0.2592 |
| Phenol red | 5.248~7.872. |

2. The medium according to claim 1, further comprising 0.001 to 220 mg/L of sodium pyruvate.

3. The medium according to claim 1, further comprising 0.000692 to 0.00348 of sodium selenite.

4. The medium according to any one of claims 1 to 3, further comprising 2.5 to 4.5 g/L HEPES, and NaHCO$_3$ in an amount required for an adjustment to desired pH.

5. A method for culturing ES cells comprising culturing ES cells with the medium of claim 1.

* * * * *